US00PP34694P2

(12) United States Plant Patent
Sharoni et al.

(10) Patent No.: US PP34,694 P2
(45) **Date of Patent: *Oct. 25, 2022**

(54) ***PORTULACA* PLANT NAMED 'DPORMPZPUP'**

(50) Latin Name: *Portulaca oleracea*
Varietal Denomination: DPORMPZPUP

(71) Applicant: Danizger 'DAN' Flower Farm, Beit Dagan (IL)

(72) Inventors: Pazit Sharoni, Beit Dagan (IL); Amir Zuker, Beit Dagan (IL); Gavriel Danziger, Beit Dagan (IL)

(73) Assignee: Danziger "Dan" Flower Farm

( * ) Notice: Subject to any disclaimer, the term of this patent is extended or adjusted under 35 U.S.C. 154(b) by 0 days.

This patent is subject to a terminal disclaimer.

(21) Appl. No.: 17/571,093

(22) Filed: Jan. 7, 2022

Related U.S. Application Data

(63) Continuation of application No. 17/319,954, filed on May 13, 2021.

(51) Int. Cl.
*A01H 5/02* (2018.01)
*A01H 6/00* (2018.01)

(52) U.S. Cl.
USPC ..... Plt./471
CPC ..... *A01H 6/00* (2018.05)

(58) Field of Classification Search
USPC ..... Plt./471; 800/298, 295, 260
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Portulaca* plant named 'DPORMPZPUP' is disclosed, characterized by large, vivid purple flowers, dark green foliage, and a controlled, semi-trailing habit. The new variety is a *Portulaca*, typically produced as an ornamental plant.

2 Drawing Sheets

Figure 1:
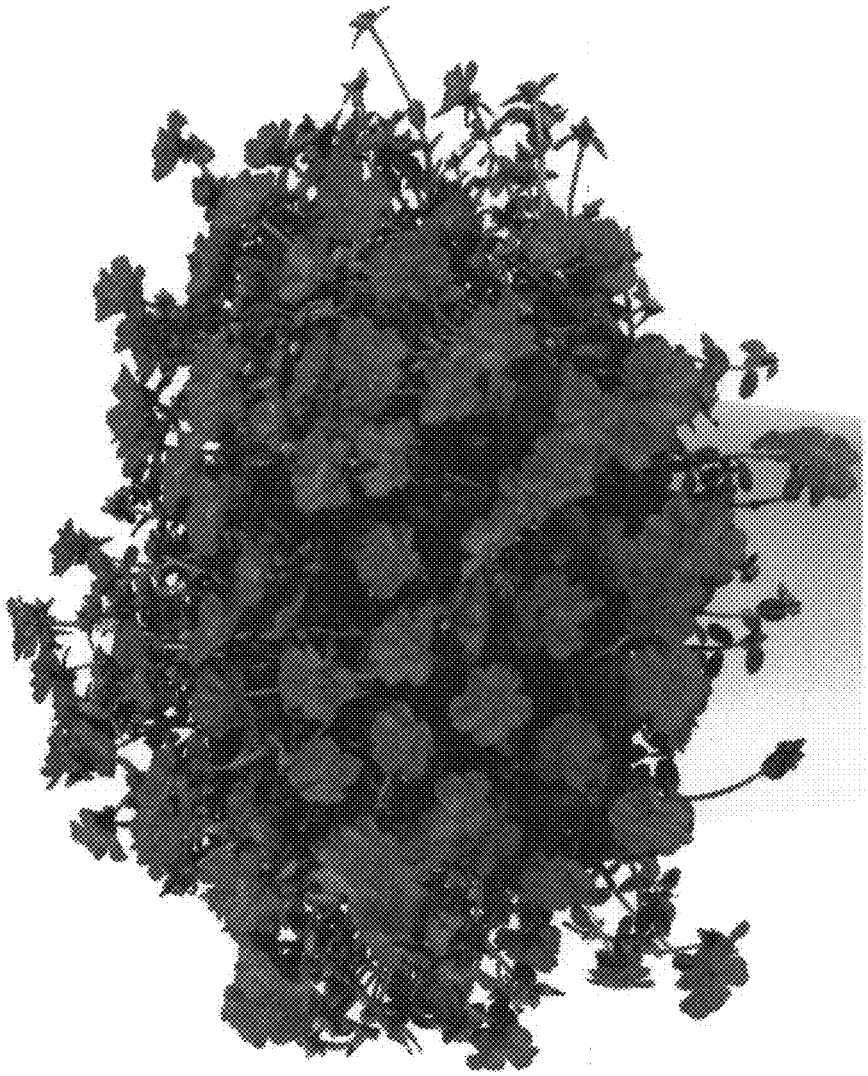

Latin name of the genus and species: *Portulaca oleracea.*
Variety denomination: 'DPORMPZPUP'.

BACKGROUND OF THE INVENTION

The new *Portulaca* cultivar is a product of a planned breeding program conducted by the inventors, Pazit Sharoni, Amir Zuker and Gavriel Danziger in Moshav Mishmar Hashiva, Israel. The objective of the breeding program was to produce useful new *Portulaca* varieties for ornamental horticultural production. The open-pollination resulting in this new variety was made during 2016.

The seed parent is the unpatented, propriety variety referred to as *Portulaca* 'PT-16-1441'. The pollen parent is unidentified. The new variety was discovered in July of 2017 by the inventors in a group of seedlings resulting from the 2016 open pollination, in a greenhouse in Moshav Mishmar Hashiva, Israel. After selection of the new variety, extensive confidential testing has been performed to determine and define the desirable characteristics of the new variety.

Asexual propagation of *Portulaca* 'DPORMPZPUP' was performed by vegetative basal cuttings during August of 2017 at a research greenhouse in Moshav Mishmar Hashiva, Israel.

SUMMARY OF THE INVENTION

The cultivar 'DPORMPZPUP' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPORMPZPUP'. These characteristics in combination distinguish 'DPORMPZPUP' as a new and distinct *Portulaca* cultivar:

1. Controlled, semi-trailing habit.
2. Large flowers.
3. Vivid purple flower color.
4. Dark green foliage.
5. Freely branching habit.

PARENT COMPARISON

Plants of 'DPORMPZPUP' are similar in some horticultural characteristics to the seed parent. The new variety, however, differs in the following:

1. Flowers of the new variety are solid, vivid purple; flowers of the seed parent are dark pink and white.
2. Flowers of the new variety are more open and nearly flat; flowers of the seed parent are more conical to funnel-shaped.
3. Flowers of the new variety are larger than those of the seed parent.

Comparison with the pollen parent is unavailable, as this variety resulted from an open pollination.

COMMERCIAL COMPARISONS

Plants of 'DPORMPZPUP' are similar in some horticultural characteristics to the variety *Portulaca* 'Nano Purple', unpatented. The new variety, however, differs in the following:

1. This comparator has a more compact and dense habit than 'DPORMPZPUP'.
2. The flower color of this comparator is bright pink with a yellow eye; flowers of 'DPORMPZPUP' are solid, vivid purple.

3. Foliage color of this comparator is brighter green than foliage of 'DPORMPZPUP'.

Plants of 'DPORMPZPUP' are similar in some horticultural characteristics to the variety *Portulaca* 'Pazzaz Bright Purple', unpatented. The new variety, however, differs in the following:

1. Foliage color of this comparator is brighter green than foliage of 'DPORMPZPUP'.
2. 'DPORMPZPUP' produces larger flowers than this comparator.
3. 'DPORMPZPUP' produces a brighter purple flower than this comparator.

BRIEF DESCRIPTION OF THE PHOTOGRAPHS

The accompanying photograph in FIG. 1 illustrates in full color a typical plant of 'DPORMPZPUP' at about 8 weeks of age, grown in a 19 cm pot.

Figure 2:
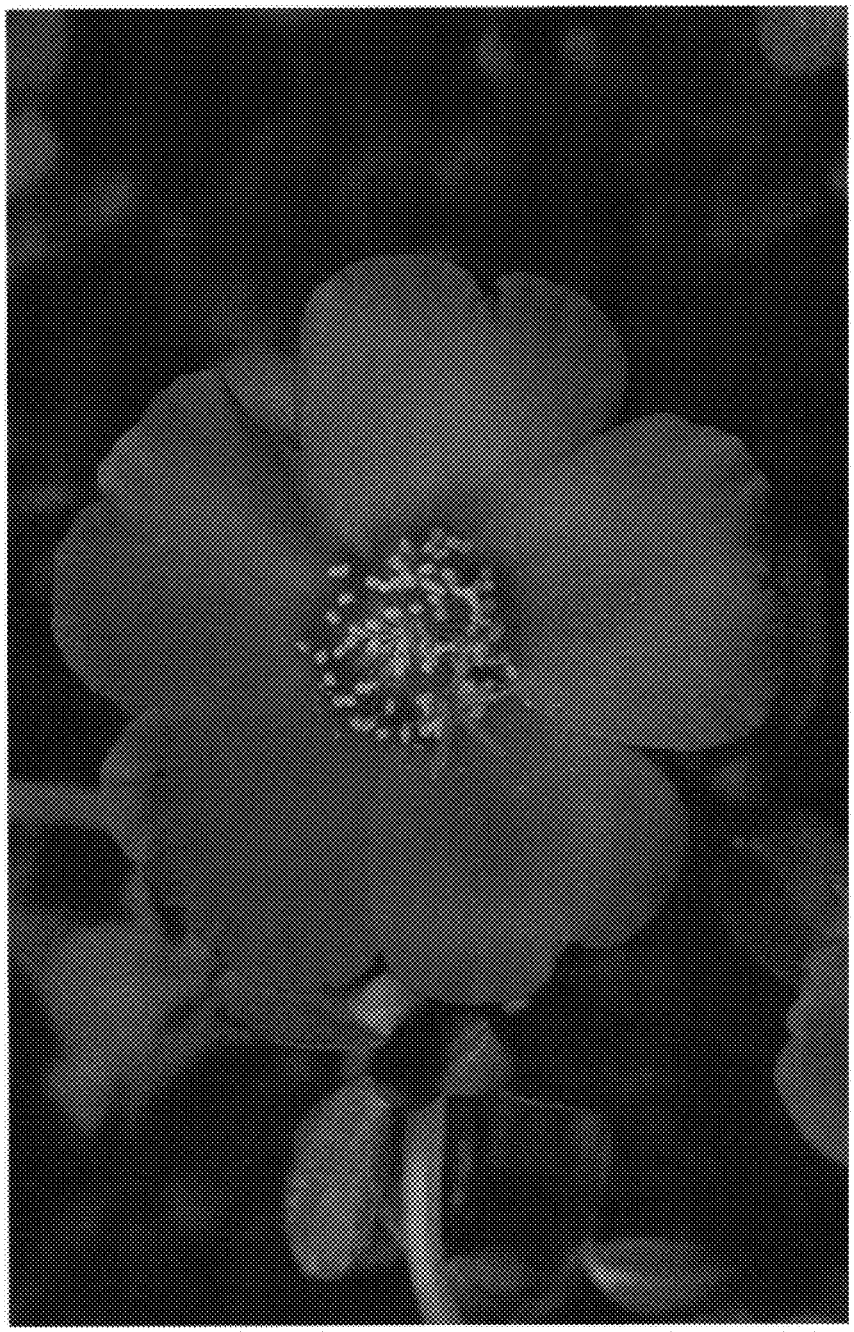

FIG. 2 illustrates a close-up view of a typical flower of the new variety.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPORMPZPUP' plants grown outdoors in Moshav Mishmar Hashiva, Israel, under natural lighting. Measurements were taken during Spring. The growing temperature ranged from approximately 24° C. to 38° C. during the days, 12° C. to 26° C. during the nights. Measurements and numerical values represent averages of typical plant types.

Botanical classification: *Portulaca oleracea* 'DPORMPZPUP'.

PROPAGATION

Time to initiate rooting: Vegetative cuttings.
Root description: 10 to 12 days at approximately 24° C.
Root description: Fine, fibrous; close to RHS Yellow-White 158C in color, freely branching.

PLANT

Growth habit: Semi-trailing.
Pot size of plant described: 19 cm.
Height: About 18 cm.
Plant spread: About 25 cm radius.
Growth rate: Medium vigor.
Branching characteristics:
Length of lateral branches: 25 cm.
Diameter of lateral branches: 0.5 cm.
Quantity of lateral branches: About 10 per main stem.
Characteristics of primary lateral branches:
- *Diameter.*—About 0.35 cm.
- *Color.*—Tip near RHS Yellow-Green 144A; base near RHS Red-Purple 59B (anthocyanin coloration).
- *Texture.*—Glabrous.
- *Strength.*—Moderately strong.

Internode length: 2.5 to 3 cm.
Age of plant described: Approximately 60 days from a rooted cutting.

FOLIAGE

Leaf:
- *Arrangement.*—Alternate, simple.
- *Quantity.*—Approximately 15 per branch.
- *Average length.*—2.5 to 3.6 cm.
- *Average width.*—1.5 to 2 cm.
- *Pubescence.*—None.
- *Shape.*—Obovate.
- *Apex.*—Rounded, slightly mucronate.
- *Base.*—Cuneate.
- *Margin.*—Entire.
- *Texture.*—Smooth and succulent, both sides.
- *Aspect.*—Straight, occurring at about 45-80°.
- *Color.*—Young, Upper side: Near RHS Green 137B. Young, Under side: Near RHS Green 138B. Mature, Upper side: Near RHS Green N137C, margins flushed near Purple N79B. Mature, Under side: Near RHS Green 138C, margins flushed near Purple N79C.
- *Venation.*—Indistinguishable from leaf blade.

Petiole:
- *Length.*—About 1.5 mm.
- *Diameter.*—About 1.5 mm.
- *Color.*—Near RHS Yellow-Green 144B.
- *Texture.*—Smooth, glabrous.

FLOWER

Natural flowering season: Spring to Fall.
Days to flowering from rooted cutting: About 4 weeks to the first flowers.
Inflorescence and flower type and habit: Single flower, abundant flowering.
Rate of flower opening: About 3 days from bud to fully opened flower.
Flower longevity on plant: About 1 day.
Persistent or self-cleaning: Self-cleaning.
Bud:
- *Buds per lateral stem.*—15 to 20.
- *Shape.*—Ovoid.
- *Length.*—1 to 1.3 cm.
- *Diameter.*—0.7 cm.
- *Color.*—Near RHS Yellow-Green 144B; tip anthocyanin flushed near Red-Purple 61A.

Flower size:
- *Diameter.*—About 5.3 cm.
- *Depth.*—About 2 cm.

Corolla/petals:
- *Arrangement.*—5 petals merged/fused at the base.
- *Length.*—2.6 cm.
- *Width.*—2.2 cm.
- *Quantity.*—5 petals.
- *Texture.*—Smooth, glabrous.
- *Apex.*—Emarginate to retuse.
- *Shape.*—Obovate with a cuneate base.
- *Margin.*—Entire.
- *Aspect.*—Mostly flat, upper margin slightly rolled down.
- *Color.*—When Opening, Upper Surface: RHS Purple N78A, entirely flushed Red-Purple N74A. When Opening, Lower Surface: RHS Red-Purple N74B. Fully Opened, Upper Surface: RHS Purple N78A, entirely flushed Red-Purple N74A. Fully Opened, Lower Surface: RHS Red-Purple N74A.

Calyx/sepals:

*Quantity per flower.*—2.

*Shape.*—Fused into a tubular calyx. Pointed apex.

*Length.*—1 cm.

*Width.*—1 cm.

*Apex.*—Acute.

*Base.*—Fused.

*Margin.*—Entire.

*Texture.*—Glabrous.

*Color.*—Upper Surface: RHS Yellow-Green 144B, anthocyanin flushed Red-Purple 60B. Lower Surface: Near RHS Yellow-Green 144B.

Peduncles: None.

Fragrance: None.

REPRODUCTIVE ORGANS

Androecium:

Stamens:

*Number.*—Many, about 60.

*Filament length.*—Approximately 0.6 cm.

Anthers:

*Shape.*—Oval.

*Length.*—About 0.8 mm.

*Color.*—Near RHS Yellow-Orange 14A.

*Pollen.*—Color: RHS Yellow-Orange 17A. Quantity: Abundant.

Gynoecium:

Pistil:

*Number.*—1.

*Length.*—1 cm.

*Style.*—Length: 0.8 cm. Color: Base near RHS Yellow 12A, tip near Red-Purple 61B.

*Stigma.*—Shape: Six branched stigma. Color: Near RHS Red-Purple 61B. Ovary Color: Near RHS Yellow-Green 144B.

OTHER CHARACTERISTICS

Seeds and fruits: Seeds are minute and dark grey with a circular shape.

Disease/pest resistance: Neither resistance nor susceptibility observed. *Portulaca* is not typically susceptible to many diseases and pests. The most common diseases being typical root rots from over watering, or black stem, *Dichotomophthora portulaca*. The most common pest of *Portulaca* is Aphid.

Temperature tolerance: Will not tolerate temperatures below 7° C. High temperature tolerance near 40° C.

What is claimed is:

1. A new and distinct cultivar of *Portulaca* plant named 'DPORMPZPUP' as herein illustrated and described.

* * * * *